(12) United States Patent
Boese

(10) Patent No.: US 8,099,153 B2
(45) Date of Patent: Jan. 17, 2012

(54) METHOD FOR THREE-DIMENSIONAL LOCALIZATION OF AN INSTRUMENT FOR AN INTERVENTIONAL ACCESS AND ASSOCIATED DEVICE

(75) Inventor: Jan Boese, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 1003 days.

(21) Appl. No.: 12/070,479

(22) Filed: Feb. 19, 2008

(65) Prior Publication Data
US 2008/0208040 A1 Aug. 28, 2008

(30) Foreign Application Priority Data
Feb. 26, 2007 (DE) .......................... 10 2007 009 177

(51) Int. Cl.
A61B 6/00 (2006.01)
G06K 9/00 (2006.01)
(52) U.S. Cl. .............................. 600/424; 378/87; 378/62
(58) Field of Classification Search .................... 382/128
See application file for complete search history.

(56) References Cited

U.S. PATENT DOCUMENTS

| 5,729,584 | A | * | 3/1998 | Moorman et al. | 378/146 |
|---|---|---|---|---|---|
| 6,351,513 | B1 | * | 2/2002 | Bani-Hashemi et al. | 378/8 |
| 6,389,104 | B1 | * | 5/2002 | Bani-Hashemi et al. | 378/98.12 |
| 6,542,770 | B2 | * | 4/2003 | Zylka et al. | 600/424 |
| 6,614,871 | B1 | * | 9/2003 | Kobiki et al. | 378/20 |
| 7,590,442 | B2 | * | 9/2009 | Boese et al. | 600/424 |
| 7,680,528 | B2 | * | 3/2010 | Pfister et al. | 600/429 |
| 2003/0123614 | A1 | * | 7/2003 | Silver et al. | 378/146 |
| 2008/0234570 | A1 | * | 9/2008 | Gerard et al. | 600/424 |

FOREIGN PATENT DOCUMENTS
DE 694 19 134 T2 1/2000
DE 10 2005 059 300 A1 6/2006

* cited by examiner

Primary Examiner — Long V. Le
Assistant Examiner — Lawrence Laryea

(57) ABSTRACT

The invention relates to a method for three-dimensional localization of an instrument for an interventional access, comprising: creating a three-dimensional image recording covering a region of the intervention and surroundings; determining local attenuation values of the three-dimensional image recording by x-ray absorption characteristics; recording a two-dimensional image recording covering the region of the intervention and surroundings; determining an x-ray intensity at an x-ray sensor arranged on the instrument; localizing the x-ray sensor in the two-dimensional image recording based on the x-ray intensity; summing the local attenuation values along a virtual x-ray path passing through the x-ray sensor in the three-dimensional image recording; identifying a point on the virtual x-ray path where the attenuation sum corresponds to the x-ray intensity at the x-ray sensor; and determining a three-dimensional position of the point corresponding to the three-dimensional position of the x-ray sensor on the instrument.

20 Claims, 2 Drawing Sheets a b c d e f

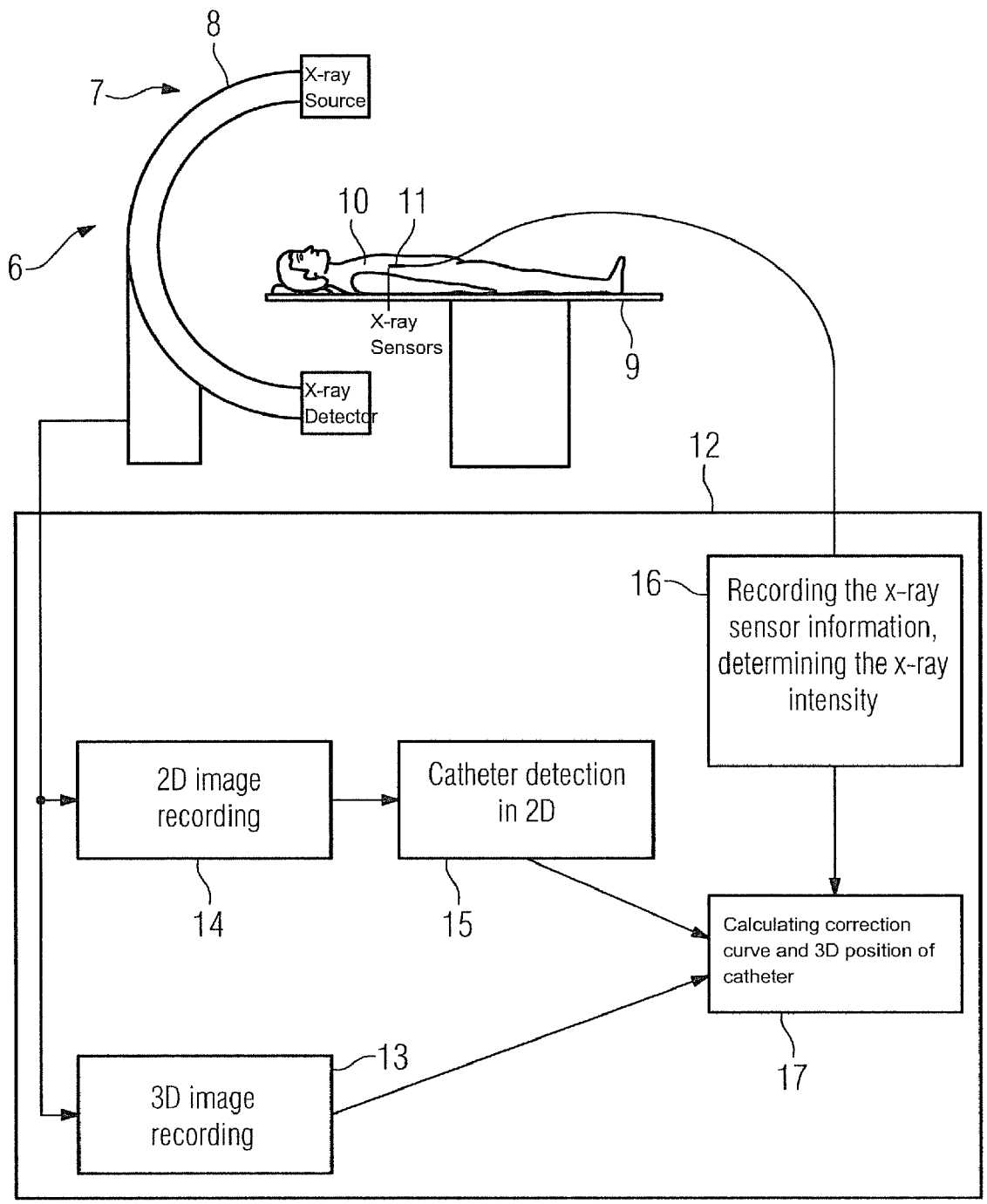

METHOD FOR THREE-DIMENSIONAL LOCALIZATION OF AN INSTRUMENT FOR AN INTERVENTIONAL ACCESS AND ASSOCIATED DEVICE

CROSS REFERENCE TO RELATED APPLICATIONS

This application claims priority of German application No. 10 2007 009 177.1 filed Feb. 26, 2007, which is incorporated by reference herein in its entirety.

FIELD OF THE INVENTION

The invention relates to a method for three-dimensional localization of an instrument for an interventional access, in particular of a catheter or guide wire or stent, in the context of x-ray monitoring of the intervention by means of two-dimensional image recordings, and an associated device for three-dimensional localization of an instrument for an interventional access.

BACKGROUND OF THE INVENTION

A multiplicity of interventional procedures are performed, e.g. radiological or cardiological interventions, in which vascular diseases are to be diagnosed or treated. These interventional methods are often accompanied by image-based monitoring. In this case, the image-based monitoring is frequently performed by an x-ray system, e.g. a C-arm angiography system. Using the x-ray images which are produced in this way it is possible to show the position of the instruments that are used for the intervention, wherein said instruments can comprise catheters, guide wires, stents and other instruments.

However, the disadvantage of using monoplanar x-ray systems or generating merely two-dimensional image recordings is that the position of the relevant instruments can only be determined in two dimensions, i.e. in the plane of the image. Depth information which would allow three-dimensional positioning is not available.

The knowledge of the three-dimensional position of instruments is often advantageous, however, e.g. if there exists previously recorded three-dimensional image data by means of which the position of the instrument could be represented in three dimensions as a superimposition, for example. Such three-dimensional image data might exist as a result of e.g. magnetic resonance recordings, CT recordings or a previously performed angiography. If information relating to the three-dimensional position of instruments were available, navigation in the context of the intervention method would be simplified considerably.

Until now, there have been essentially two approaches which allow a three-dimensional localization of instruments.

These include firstly the so-called electromagnetic localization systems in which the position of the instrument is determined by means of a receiving coil, at the tip of the instrument, picking up signals from typically three transmitting coils which are located outside of the patient. By means of triangulation it is then possible to determine the three-dimensional position of the instrument.

In this type of configuration, however, it can be problematic that considerable additional hardware must be integrated into the system as a result of the transmission and reception electronics and the respective coils. In addition, the size of the receiving coils is not insignificant. Metal objects and the like can also cause interference in the electromagnetic field.

A further approach consists of three-dimensional localization using x-rays, in which at least two two-dimensional x-ray images are recorded from different directions, preferably simultaneously by means of a biplanar x-ray system. It is then possible to calculate a three-dimensional position of the instrument from the two-dimensional positions that can be derived from the images. In comparison with the electromagnetic method, this offers the advantage that any instruments can be used and that no further hardware is required apart from the x-ray system.

Using this approach, however, the problem exists that two x-ray images are necessary. This requires an expensive biplanar x-ray system. Alternatively, the two images can be recorded one after the other by changing the angulation of a C-arm. As a result of this, however, the refresh rate of the localization is significantly reduced in comparison with the typical image rate of approximately 15 images per second. The method can therefore no longer be used for the purpose of accompanying a navigation in real time.

SUMMARY OF THE INVENTION

The invention therefore addresses the problem of specifying a method which is improved in this regard for three-dimensional localization of an instrument.

This problem is solved by a method of the type described in the introduction, which method has the following steps:

creating at least one three-dimensional image recording whose volume covers the region affected by the intervention and its surroundings, using an x-ray image recording device for determining local attenuation values which are determined by the x-ray absorption characteristics, creating at least one two-dimensional image recording using the or a further x-ray image recording device and essentially simultaneously determining the x-ray intensity at least one x-ray sensor which is arranged on the instrument, localizing in two dimensions the x-ray sensor in the at least one two-dimensional image recording by means of a computing device, for a virtual ray from the x-ray source through the two-dimensionally localized x-ray sensor to the x-ray detector in the volume of the at least one three-dimensional image recording, summing the local attenuation values along the ray path, by means of the computing device, for the purpose of identifying the point on the ray at which the attenuation sum corresponds to the amount which, given a known intensity of the x-ray source, results in the determined x-ray intensity at the x-ray sensor, and determining the three-dimensional position of the identified point, which position corresponds to the three-dimensional position of the at least one x-ray sensor on the instrument, by means of the computing device.

The sequence of the individual steps can vary if necessary. For example, the three-dimensional image recording can be prepared using an image recording device which is also available during the monitored intervention, such that the three-dimensional recordings can be created during the intervention.

The invention therefore provides for the creation, first or later, of a three-dimensional image recording which shows a region that is affected by the e.g. cardiological or radiological intervention, specifically e.g. the region of the heart in the case of a cardiological intervention. The image recording also shows a surrounding region, in order subsequently to have available the required information concerning the attenuation values along a ray path from the x-ray source to the detector. The three-dimensional image recording can be created using different methods. In order that the local attenuation values are visible or can be identified it is necessary to provide an x-ray image recording, from which the attenuation values in the volume can be inferred on the basis of the x-ray absorption characteristics which are manifested in the different brightness or intensity of the individual image points.

Subsequently or additionally, at least one two-dimensional image recording is created using this or another x-ray image recording device. In this case, this two-dimensional image recording is typically the two-dimensional image recording for x-ray monitoring of the interventional access which is taking place at the same time.

The interventional access itself, specifically e.g. the introduction of a catheter into the heart, is not the subject matter of the method according to the invention. The method according to the invention relates solely to the localization, i.e. a purely technical measuring operation, which typically takes place under the guidance of a technician or scientist.

This measuring operation as such is based solely on the analysis of x-ray images or sensor data, and therefore no monitoring by a doctor of other medical personnel is required for the method according to the invention. The doctor can instead concentrate fully on the intervention, for which the three-dimensional position of the instrument is additionally available to him or her as a result of the method according to the invention.

At essentially the same time as the two-dimensional image recording, the x-ray intensity is determined at least one x-ray sensor which is arranged on the instrument. The instrument which must be localized is therefore equipped with an x-ray sensor, by means of which the localization is simplified as described in the following.

On the basis of the two-dimensional image recordings or the one two-dimensional image recording, the x-ray sensor can now be localized by means of a computing device which has been specifically designed for this purpose and which also controls the three-dimensional and two-dimensional image recording if applicable. Corresponding image processing programs or corresponding image processing means are available on the computing device for this purpose. If necessary, the computing device can have access to external software which allows corresponding image processing e.g. using pattern recognition and coordinate assignment. According to the invention, the x-ray sensor is usually attached to the tip of the instrument and consequently the tip of the instrument is located in two dimensions using the x-ray sensor. Of course, the x-ray sensor can also be attached at a different place on the instrument.

For a virtual ray from the x-ray source through the two-dimensionally localized x-ray sensor to the x-ray detector in the volume of the at least one three-dimensional image recording, the computing device then performs a summation of the local attenuation values along the ray path for the purpose of identifying the point on the ray at which the attenuation sum corresponds to the amount which, given a known intensity of the x-ray source, results in the measured or determined intensity at the x-ray sensor.

Finally, using corresponding calculation software, the computing device determines the three-dimensional position of the identified point, which position corresponds to the three-dimensional position of the at least one x-ray sensor on the instrument.

For the purpose of determining the missing depth information which is required in addition to the two-dimensional localization for a three-dimensional localization, the intensity of the x-ray radiation at the x-ray tubes is therefore identified or supplied to the calculation on the basis of the known x-ray parameters.

A virtual ray is traced through the three-dimensional volume, which can be e.g. a volume from a computer tomography recording, through the point of the x-ray sensor or the tip of the instrument, or another location or point of the instrument which has been assigned to the sensor. This ray runs from the x-ray tube through the sensor to the detector of the system.

The local attenuation values along the ray path are summed or integrated until the sum or the integral value corresponds exactly to the attenuation which, from the x-ray intensity of the x-ray tube, would generate the actual measured intensity at the x-ray sensor. The point at which this threshold value is reached then corresponds exactly to the three-dimensional localization of the catheter tip, or of another location of the instrument at which the x-ray sensor is arranged.

In the case of a plurality of sensors on the instrument, a plurality of ray paths can be traced accordingly. The information relating to the attenuation values is obtained from the three-dimensional volume recording in this case, wherein it is also possible if applicable to use a plurality of three-dimensional volume recordings which need not necessarily have been created before the monitoring of the intervention by means of the two-dimensional image recordings. As a rule, however, the three-dimensional image recordings are created beforehand using a separate x-ray system, e.g. a computer tomograph. During the intervention, the monitoring then takes place using a simpler x-ray system such as a monoplanar C-arm.

The invention therefore allows the instrument, e.g. a guide wire or a stent, to be localized exactly in three dimensions. In order to achieve this, in addition to the original three-dimensional image data record, only one further two-dimensional image data record is effectively required at the current instant for the localization. This two-dimensional image recording, which is typically made repeatedly during an intervention for observation, is then sufficient to identify the missing depth information at the relevant instant by means of combination with the x-ray intensity that is reported by the x-ray sensor and with reference to the three-dimensional image data record. In this case, the three-dimensional image recording is only required for the purpose of determining the 3D distribution of the x-ray attenuation values. During the actual monitoring of the intervention, i.e. during the intervention itself, it is not necessary to make any three-dimensional image recordings.

The method according to the invention can therefore allow realtime monitoring of an intervention even with a monoplanar x-ray system.

Depending on the determined three-dimensional position of the x-ray sensor, the instrument and/or a point of the instrument which is assigned to the at least one x-ray sensor in the at least one two-dimensional image recording and/or the at least one three-dimensional image recording can be displayed at an image output means.

For example, if a catheter or a guide wire is equipped at its tip with one or more x-ray sensors, the corresponding 3D position of the tip can be included in a two-dimensional or three-dimensional image. Such an inclusion can take place in the volume image from the computer tomography, for example. When using a plurality of sensors it is possible to infer the form of the whole instrument, such that a representation of e.g. the whole stent is possible in a superimposition on the two-dimensional or three-dimensional image recording. By repeating the localization method, the position can be actively identified in real time in each case and optionally displayed on a monitor or a screen.

The or at least one three-dimensional image recording can be created using a computer tomography device and/or a biplanar x-ray device and/or a monoplanar x-ray device which is embodied for creating rotation angiography recordings, in particular using a C-arm device.

In this case it is also possible for a previously recorded computer tomography recording to be registered with the x-ray system for monitoring the intervention. If applicable it is also possible to create image recordings from a combination of different recording methods. In the case of computer tomography recordings and recordings of a biplanar system, the creation of three-dimensional recordings is particularly easy. In the case of a monoplanar x-ray device it is optionally possible to create rotation angiography recordings by changing the angulation of the C-arm correspondingly. In this case, however, it must be noted that a corresponding time delay must be taken into consideration during the creation of the different image recordings due to the change in the position of the C-arm.

The at least one two-dimensional image recording can be created using a monoplanar x-ray device. In this case the particular advantage of the inventive method is evident, in that a three-dimensional localization is actually possible on the basis of a single x-ray image from a monoplanar C-arm system, provided just one 3D distribution of the x-ray attenuation values is present. In this instance the instrument is first localized in two dimensions only, whereupon the missing depth information is determined from the measured x-ray intensity at the x-ray sensor and the x-ray attenuation values in the volume.

Even using a simple monoplanar system, therefore, localization in real time is possible. Further or additional hardware is not required, in particular no expensive electronics or associated coils.

The required x-ray sensors are very small and hence easy to integrate into small instruments such as catheters.

Furthermore, according to the invention, the or at least one two-dimensional image recording can be created using a computer tomography device and/or a biplanar x-ray device and/or a monoplanar x-ray device which is embodied for creating rotation angiography recordings, in particular using a C-arm device. The two-dimensional image recording or the image recording which is prepared for the purpose of monitoring can therefore also be created using a biplanar x-ray device or a monoplanar system which is embodied for recording rotation angiography recordings. Of course, computer tomographs or other x-ray systems not specified here can also be used for the two-dimensional image recording or the plurality of two-dimensional image recordings.

Furthermore, the or at least one three-dimensional image recording and the or at least one two-dimensional image recording can be recorded using the same x-ray device or x-ray image recording device. The registration is simplified in this case, since transformations are no longer required, or can be avoided or simplified. It is particularly advantageous if both the three-dimensional and the two-dimensional image recordings are created using a monoplanar system which is embodied for recording rotation angiography recordings. In such a case it is possible to dispense with a supplementary computer tomography system or similarly expensive x-ray systems.

According to the invention it is possible to use at least one x-ray sensor which is arranged at the tip and/or in the region of the tip and/or in the region of the front part of the instrument. In particular, the localization of the tip of the instrument is usually required. This applies particularly in the case of catheters. Furthermore, however, it can also be helpful to see a complete front region of an instrument, e.g. a stent in the case of a balloon catheter system featuring such a stent or a self-unfolding stent.

If applicable, x-ray sensors can be arranged over the entire length of the instrument if the inventive method is to allow a localization for a particularly complicated interventional access or a structurally complex instrument. If applicable, a plurality of x-ray sensors can be arranged in the region of the tip or in a front region of the instrument.

According to the invention, therefore, it is possible to use a plurality of x-ray sensors arranged on the instrument, in particular two to five x-ray sensors. With the aid of two x-ray sensors, directional information can be obtained. In the case of a plurality of x-ray sensors, data or measurement information is also obtained in relation to a curvature of the corresponding region of the instrument, e.g. the tip of a catheter in the case of coronary interventions.

The use of a plurality of x-ray sensors arranged on the instrument offers the advantage that a consistency check of the attenuation values can be carried out by the computing device on the basis of the x-ray signals.

This allows the localization accuracy in the end result to be improved and artifacts to be excluded. Such artifacts can occur e.g. due to errors in the three-dimensional image data record or calculation inaccuracies when determining said image data record or when deriving the attenuation values. Given a plurality of x-ray sensors, therefore, not only is it possible to determine the form of the instrument, which can be important for the purpose of navigation, in the context of the method according to the invention, but consistency conditions for the attenuation are also obtained which can be used as new boundary conditions for improving the localization.

At least one x-ray photodiode, this being arranged on the instrument, can be used as an x-ray sensor.

Such photodiodes have a size of approximately 100 μm per dimension. By comparison, the wires of coils used for electromagnetic localization methods have thicknesses which are normally approximately 2 mm and no less than 0.3 mm at present. Consequently, it is significantly easier to integrate an x-ray sensor, e.g. the aforementioned photodiode, in small instruments than it is to integrate receiving coils in electromagnetic systems.

At least one x-ray sensor can transmit its sensor signal or signals to the computing device via at least one lead and/or wirelessly.

The x-ray signal or x-ray signals which are picked up during the course of the localization method or during the intervention monitoring are therefore transmitted to the computing device via leads or using a radio technique. It is also possible additionally to use both transmission principles if applicable. A wireless transmission, which can essentially follow the principle of radio frequency identification, is particularly suitable in the case of very small instruments. An energy supply can also be provided in this way.

If leads are used, their design must be correspondingly thin in order that they do not hamper the interventional access. By virtue of the x-ray sensors it is possible to measure the local x-ray intensity from outside at any time with the aid of the leads or the wireless transmission technique.

According to the invention, for the purpose of error detection, the attenuation values along the ray path can be summed for at least one further virtual ray, which optionally does not run in the vicinity of the instrument, in the volume of the at least one three-dimensional image recording, and a or the value which is calculated therefrom by the computing device for the attenuation of the intensity can be compared with an intensity or the intensity which is measured at an x-ray detector of the x-ray image recording device. On the basis of a comparison of a plurality of measured and calculated values of the intensities, the computing device can determine a correction curve which assigns a measured intensity to each calculated intensity.

As a result of this it is possible to carry out a calibration method which resolves the problem that the attenuation values which are calculated along the virtual ray vary in practice from the values that are measured at the x-ray sensor. Such variations are caused e.g. by inaccuracies in the attenuation values or in a C-arm computer tomography recording (cf. Hounsfield accuracy). Other possible causes include difficulties in the precise calculation of the x-ray intensity of the x-ray tube in the case of fluctuating x-ray parameters and measurement inaccuracies of the x-ray sensor.

In order to counter these problems, in addition to the one virtual ray through the x-ray sensor, other rays which preferably do not lie in the vicinity of the instrument volume but possibly also rays in the vicinity of the instrument are traced through the three-dimensional volume, i.e. e.g. the computer tomography volume. The intensities are summed. The calculated attenuated intensity should correspond to the radiation measured at the x-ray detector of the x-ray system. If this is not the case, a correction is produced which can be included in the correction curve or can be used in conjunction with further corrections to determine a correction curve.

With reference to a comparison of a plurality of measured and calculated values of the intensities, i.e. on the basis of planned/actual pairs, it is therefore possible to determine a correction curve which assigns a measured intensity to each calculated intensity.

For the three-dimensional image recording device it is therefore possible to calculate the intensities for the virtual rays in each case, and to compare said intensities with the actual measured intensities or the actual radiation profiles which are defined by these, in order thus to reveal errors in the attenuation values, resulting e.g. from the calculation of the x-ray intensity.

Furthermore, the invention relates to a device for three-dimensional localization of an instrument for interventional access, in particular of a catheter or guide wire or stent, in the context of x-ray monitoring of the intervention by means of two-dimensional image recordings, comprising at least an x-ray image recording device, in particular a monoplanar x-ray device which is optionally embodied for creating rotation angiography recordings, and a computing device which is embodied for carrying out the method as claimed in one of the preceding claims.

The device therefore features a computing device and at least one x-ray image recording device.

The x-ray image recording device is preferably a monoplanar x-ray device, in particular a C-arm system, by means of which two-dimensional image recordings can be created for monitoring an interventional access, but which can optionally also allow a three-dimensional data recording in the context of a rotation angiography.

In such a case, rotation angiography recordings can be created, e.g. before the actual intervention, which depict in three dimensions a region that is to be treated during the course of the intervention and a surrounding region. Rays can be traced through this three-dimensional volume from the three-dimensional source to the detector, wherein in the case of such a monoplanar system which is capable of rotation angiography, the three-dimensional ray source corresponds to the ray source for the creation of the two-dimensional recordings, and the position of ray source and ray detector is only adapted in the context of changing the angulation.

If applicable, the device can feature a further x-ray image recording device which is provided specially for creating the three-dimensional image recordings which are subsequently registered with the image recording device for the two-dimensional image recordings. The further image recording device can be a computer tomograph, whose three-dimensional recordings for the localization are used for the purpose of determining the attenuation values along the path of the virtual rays.

From the two-dimensional image recording of the x-ray image recording device of the device for three-dimensional localization of the instrument, the position of the instrument, or of a point on the instrument which corresponds to the x-ray sensor or to which this is assigned, is initially determined in two dimensions. The missing depth information is identified with the aid of the three-dimensional image recordings by deriving the local attenuation values therefrom. These are summed along the ray path until the attenuation is reached which matches the intensity value that was identified by the x-ray sensor. From this it is possible to infer the position in the missing third dimension.

The calculation operations in the device are made possible or controlled by means of corresponding software which is stored on the computing device or can be accessed by said computing device. If necessary, provision can be made for access to externally stored software via an intranet or the internet, or an internal storage device for local software or a removable storage medium can be provided.

The intensity at the x-ray sensor is derived from the intensity of the x-ray tube or x-ray source such that this original intensity of the x-ray tube, with the exponential function to base e as an exponent, decreases with the sum of the attenuation values along the ray path, multiplied by the relevant path variation $\Delta z$.

Having knowledge of this attenuation law, according to the invention it is possible to allow realtime monitoring of an interventional procedure using three-dimensional instrument localization, by means of a simple monoplanar system.

BRIEF DESCRIPTION OF THE DRAWINGS

Further advantages, features and details of the invention are derived from the following exemplary embodiments and with reference to the drawings, in which:

FIG. 2 shows a device according to the invention for three-dimensional localization of an instrument.

DETAILED DESCRIPTION OF THE INVENTION

Figure 1:
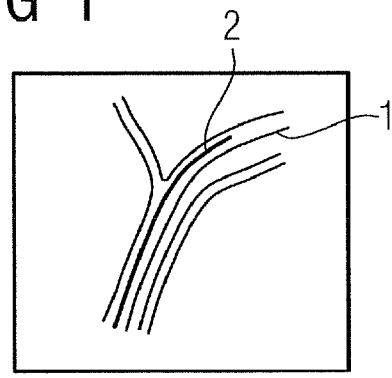
FIG. 1 shows a sequence diagram of a method according to the invention.
Figure 1:
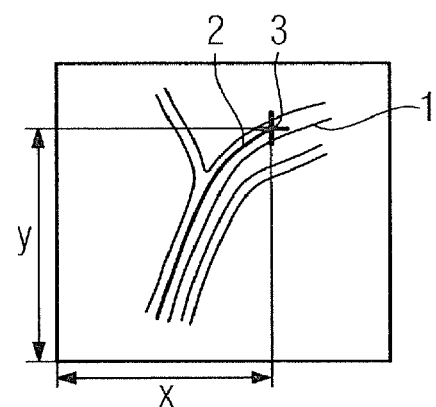
Figure 1:
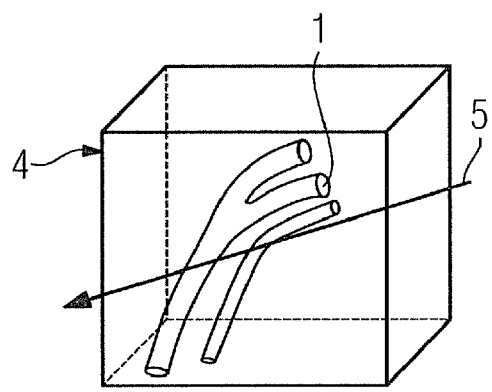
Figure 1:
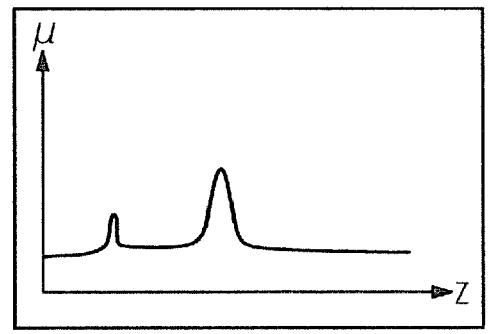
Figure 1:
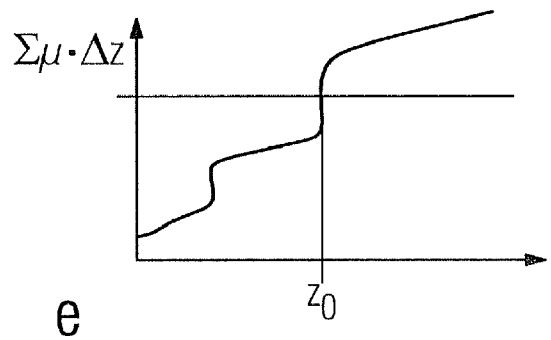
Figure 1:
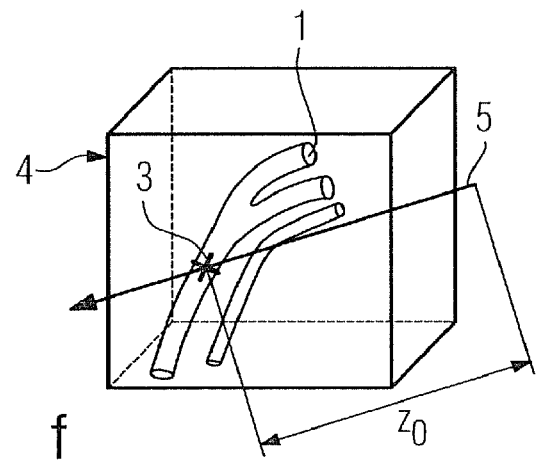

FIG. 1 represents a sequence diagram of a method according to the invention. According to step a, a two-dimensional image recording is created using an x-ray image recording device which shows the region of the intervention, here a vascular system 1 with a catheter 2, for the purpose of monitoring the interventional access.

As a result of image processing by means of a computing device, the tip of the instrument, i.e. of the catheter 2, is recognized according to step b and is illustrated here by point 3. In this context, the catheter 2 features an x-ray sensor at its tip, which sensor supplies a determined x-ray intensity to the computing device. By virtue of the x-ray sensor on the catheter 2 it is possible to measure the local x-ray intensity from the outside at any time for point 3. Point 3 is localized in the two-dimensional representation, i.e. coordinates are assigned as indicated here by the axes x and y.

For a three-dimensional localization, the depth information is now missing. For this, use is made of a three-dimensional image recording as per step c, said recording in this case being a rotation angiography recording of a monoplanar system which was also used to create the two-dimensional image recording of step a. The x-ray parameters of the image recording are known. From this, it is possible to identify the intensity of the x-ray radiation at the x-ray tube. A virtual ray 5 is passed through the volume of the rotation angiography recording 4, wherein said ray runs from the x-ray tube to the x-ray detector through point 3, which corresponds to the position of the tip of the instrument from the two-dimensional image recording as per step b and at which the x-ray sensor is situated.

In order to calculate the depth information, the attenuation values μ are observed along the ray path z as per step d. The course of these attenuation values μ is largely level outside of the vascular system 1, wherein this region is less interesting for the localization, since the instruments for the interventional access will normally be situated within the vascular system 1. When a vascular section of the vascular system 1 is encountered, the attenuation or the associated attenuation value μ shows a peak.

In accordance with step e, the local attenuation values of step d are summed until the sum which is plotted in step e corresponds to the attenuation which would generate the intensity at the x-ray sensor from the x-ray intensity of the x-ray tube. The point at which this threshold value is reached is identified as $z_0$ relative to the ray path in step e. In this case the intensity at the x-ray sensor is derived as a product of the intensity at the x-ray tubes with the exponential function to base e, with the exponent $-\Sigma\mu\cdot\Delta z$.

The three-dimensional localization of the tip of the catheter 2 identified thus is shown in step f. Point 3 from step b is therefore represented here in the volume of the three-dimensional image recording as per step c. The corresponding ray path up to point $z_0$ along the virtual ray 5 is the path which the ray covered until the threshold value as per the intensity measured at the x-ray sensor is reached.

It is therefore possible to localize the tip of the catheter 2 in three dimensions without having to create further three-dimensional image recordings, in addition to the original three-dimensional image recordings as per step c, for the purpose of monitoring the interventional access. Even using a simple monoplanar system, therefore, three-dimensional localization in real time is possible FIG. 2 shows a device 6 according to the invention for three-dimensional localization of an instrument for an interventional access. The device 6 has an x-ray image recording device 7 which is embodied as a C-arm here. In addition to the C-arm 8 comprising a ray source ray source and a ray detector, the x-ray image recording device 7 has a patient couch 9 on which a patient 10 is lying. A catheter 11 having an x-ray sensor at the catheter tip is situated in the patient 10 for the purpose of interventional access.

Also shown is a computing device 12 which, inter alia, controls the image recording operation of the x-ray image recording device 7.

The x-ray image recording device 7 is embodied as a monoplanar device in this case. Under the control of the computing device 12, which has corresponding software for this purpose, a three-dimensional image recording is created as per box 13. A two-dimensional image recording for monitoring the interventional access is also prepared as per box 14.

Using the x-ray sensor of the catheter 11 and the 2D-image recording as per box 14, two-dimensional detection of the catheter 11 is possible as per box 15. These activities are executed in the computing device 12.

The x-ray sensor at the catheter 11 receives x-ray sensor information which is also supplied to the computing device 12 as indicated by box 16. The x-ray sensor information allows the local x-ray intensity at the catheter tip to be determined from outside at all times. On the basis of the two-dimensional localization of the catheter tip at which the x-ray sensor supplying the sensor information is situated, and the three-dimensional image recording as per box 13, the three-dimensional position of the catheter can be determined as per box 17. During the monitoring of the interventional access, therefore, no three-dimensional image recordings need be created. Real-time monitoring with three-dimensional real-time localization of the catheter is nonetheless possible as described above.

For this, the computing device 12 sums the local attenuation values along a virtual ray from the x-ray tube to the detector through the two-dimensionally localized catheter tip having the x-ray sensor. The point at which the threshold value is reached, which threshold value corresponds to the attenuation that would generate the intensity at the x-ray sensor from the x-ray intensity of the x-ray tube, corresponds to the desired 3D localization of the catheter tip as per box 17.

Using the device according to the invention it is therefore possible to localize an instrument in three dimensions on the basis of a single x-ray image. The instrument, i.e. the catheter 11 here, is equipped with an x-ray sensor. A three-dimensional image is recorded. The instrument is first localized in two dimensions, the depth information being calculated from the measured local x-ray intensity at the sensor and the three-dimensional distribution of the x-ray attenuation values. Three-dimensional image recordings which were created before the actual intervention, therefore e.g. before the catheter 11 is inserted into the patient 10, are therefore sufficient. For the actual monitoring it is then only necessary to make two-dimensional image recordings, which are then sufficient to achieve a three-dimensional localization of the instrument. Such image recordings can be generated easily and quickly using a monoplanar system.

The invention claimed is:

1. A method for locating a three-dimensional position of an instrument for an intervention, comprising:
   creating a three-dimensional image recording with a volume covering a region of the intervention and surroundings;
   determining local attenuation values of the three-dimensional image recording by x-ray absorption characteristics;
   recording a two-dimensional image recording showing the instrument during the intervention by an x-ray image recording device comprising an x-ray source and an x-ray detector;
   determining an x-ray intensity at an x-ray sensor arranged on the instrument;
   localizing the x-ray sensor in the two-dimensional image recording based on the x-ray intensity;
   summing the local attenuation values along a virtual x-ray path passing through the x-ray sensor from the x-ray source to the x-ray detector in the volume of the three-dimensional image recording;
   identifying a point on the virtual x-ray path where the attenuation sum corresponds to the x-ray intensity at the x-ray sensor; and determining a three-dimensional position of the point corresponding to the three-dimensional position of the x-ray sensor on the instrument.

2. The method as claimed in claim 1, wherein the position of the instrument is displayed at an image display device.

3. The method as claimed in claim 1, wherein the x-ray image recording device is selected from the group consisting of: computer tomography device, a monoplanar x-ray device, and a biplanar x-ray device.

4. The method as claimed in claim 3, wherein the x-ray image recording device is a C-arm x-ray device.

5. The method as claimed in claim 1, wherein the three-dimensional image recording is recorded by the x-ray image recording device.

6. The method as claimed in claim 1, wherein the x-ray sensor is arranged at an area of the instrument selected from the group consisting of: a tip of the instrument, a region of the tip of the instrument, and a region of a front part of the instrument.

7. The method as claimed in claim 1, wherein a plurality of x-ray sensors are arranged on the instrument.

8. The method as claimed in claim 7, wherein a consistency of the attenuation values is checked based on the plurality of x-ray sensors.

9. The method as claimed in claim 1, wherein the x-ray sensor comprises an x-ray photodiode.

10. The method as claimed in claim 1, wherein the x-ray sensor transmits a signal via a lead or wirelessly.

11. The method as claimed in claim 1, wherein a plurality of attenuation values are summed each corresponding to one of a plurality of virtual x-ray paths which are not in a vicinity of the instrument in the volume of the three-dimensional image recording.

12. The method as claimed in claim 11, wherein the attenuation sums are compared with intensities measured at the x-ray detector.

13. The method as claimed in claim 12, wherein a correction curve is determined based on the comparison.

14. The method as claimed in claim 1, wherein the instrument is selected from the group consisting of: a catheter, a guide wire, and a stent.

15. A device for locating a three-dimensional position of an instrument for an intervention, comprising:

an x-ray image recording device comprising an x-ray source and an x-ray detector that records:
  a three-dimensional image recording with a volume covering a region of the intervention and surroundings, and
  a two-dimensional image recording showing the instrument during the intervention; and
a computing device configured to:
  determines local attenuation values of the three-dimensional image recording by x-ray absorption characteristics,
  determines an x-ray intensity at an x-ray sensor arranged on the instrument,
  localizes the x-ray sensor in the two-dimensional image recording based on the x-ray intensity,
  sums the local attenuation values along a virtual x-ray path passing through the x-ray sensor from the x-ray source to the x-ray detector in the volume of the three-dimensional image recording,
  identifies a point on the virtual x-ray path where the attenuation sum corresponds to the x-ray intensity at the x-ray sensor, and
  determines a three-dimensional position of the point corresponding to the three-dimensional position of the x-ray sensor on the instrument.

16. The device as claimed in claim 15, wherein a plurality of x-ray sensors are arranged on the instrument.

17. The device as claimed in claim 16, wherein a consistency of the attenuation values is checked based on the plurality of x-ray sensors.

18. The device as claimed in claim 15, wherein a plurality of attenuation values are summed each corresponding to one of a plurality of virtual x-ray paths which are not in a vicinity of the instrument in the volume of the three-dimensional image recording.

19. The device as claimed in claim 18, wherein the attenuation sums are compared with intensities measured at the x-ray detector.

20. The device as claimed in claim 19, wherein a correction curve is determined based on the comparison.

* * * * *